(12) United States Patent
Michel et al.

(10) Patent No.: US 8,198,468 B2
(45) Date of Patent: Jun. 12, 2012

(54) PROCESS FOR THE PREPARATION OF ENANTIOMERICALLY PURE 1-SUBSTITUTED-3-AMINOALCOHOLS

(75) Inventors: Dominique Michel, Sierre (CH); Hanspeter Mettler, Visp (CH); John McGarrity, Brig-Glis (CH)

(73) Assignee: Lonza AG, Basel (CH)

( * ) Notice: Subject to any disclaimer, the term of this patent is extended or adjusted under 35 U.S.C. 154(b) by 0 days.

(21) Appl. No.: 13/064,146

(22) Filed: Mar. 8, 2011

(65) Prior Publication Data

US 2011/0207945 A1 Aug. 25, 2011

Related U.S. Application Data

(62) Division of application No. 10/590,140, filed as application No. PCT/EP2005/001781 on Feb. 21, 2005, now Pat. No. 7,973,182.

(30) Foreign Application Priority Data

Feb. 19, 2004 (EP) .................................... 04003809
Apr. 28, 2004 (EP) .................................... 04010043

(51) Int. Cl.
*C07D 307/46* (2006.01)
(52) U.S. Cl. ....................................................... 549/479
(58) Field of Classification Search ................... 549/479
See application file for complete search history.

(56) References Cited

U.S. PATENT DOCUMENTS

| 4,515,986 A | 5/1985 | Bernhagen et al. |
| 4,948,813 A | 8/1990 | Wilkerson |
| 5,362,866 A | 11/1994 | Arnold |
| 5,491,243 A | 2/1996 | Berglund |
| 5,907,045 A | 5/1999 | Antognazza et al. |
| 6,008,412 A | 12/1999 | Ratz |

FOREIGN PATENT DOCUMENTS

| EP | 0457559 A2 | 11/1991 |
| EP | 0647648 A1 | 4/1995 |
| EP | 0926152 A1 | 6/1999 |
| EP | 0945457 A2 | 9/1999 |
| EP | 0955303 A2 | 11/1999 |
| JP | A 5070412 | 3/1993 |
| WO | WO02/40492 A1 | 5/2002 |
| WO | WO2004/005220 A2 | 1/2004 |
| WO | WO2004/005239 A1 | 1/2004 |
| WO | WO2004/005307 A1 | 1/2004 |

OTHER PUBLICATIONS

Robertson et al., J. Med. Chem., ACS, vol. 31, Jul. 1, 1988, 1412-1417.
Sakuraba et al., Chem. Pharm. Bull.,vol. 43, No. 5, 1995, 748-753.
Derwent, No. 131254, 1993, London, GB, abstract (Fuji).
Hulling et al., Chirality, 2000, 12, 26-29.
Sorbera et al., Drugs of the Future, 2000, 25(9), 907-916.
Wheeler et al., J. Labelled Comp. Radiiopharm., 1995, 36, 213-223.

*Primary Examiner* — Taofiq A Solola
(74) *Attorney, Agent, or Firm* — Hoffmann & Baron, LLP

(57) ABSTRACT

A salt of a carboxylic acid with an aminoketone of formula II.

1 Claim, No Drawings

PROCESS FOR THE PREPARATION OF ENANTIOMERICALLY PURE 1-SUBSTITUTED-3-AMINOALCOHOLS

This application is a division of U.S. application Ser. No. 10/590,140, filed on Sep. 28, 2006, now U.S. Pat. No. 7,973,182 that is a 371 U.S. national stage application of International Patent Application PCT/EP2005/001781, filed on Feb. 21, 2005, that has priority benefit of European Patent Application No. 04003809.3, filed on Feb. 19, 2004, and European Patent Application No. 04010043.0, filed on Apr. 28, 2004.

The present invention refers to a process for the preparation of enantiomerically pure 1-substituted-3-aminoalcohols, particularly of (S)-(−)- and (R)-(+)-3-N-methylamino-1-(2-thienyl)-1-propanol, which can be obtained by asymmetrically hydrogenating salts of the corresponding aminoketones and a carboxylic acid, particularly of 3-N-methylamino-1-(2-thienyl)-1-propanone and a carboxylic acid, in the presence of a catalyst comprising a transition metal and a diphosphine ligand.

(S)-(−)-3-N-Methylamino-1-(2-thienyl)-1-propanol is an intermediate for the preparation of (S)-(+)-methyl-[3-(1-naphthyloxy)-3-(2-thienyl)-propyl]-amine (duloxetine), an agent for the treatment of depression and urinary incontinence (Huiling et al. *Chirality* 2000, 12, 26-29, Sorbera et al. *Drugs of the Future* 2000, 25(9), 907-916).

Several processes for racemic (WO2004/005239) and asymmetric (Sorbera et al. below) hydrogenation of thienyl aminoketone are known, as well as processes for chiral resolution of the resulting 3-N-methylamino-1-(2-thienyl)-1-propanol (WO-A 2004/005220, WO-A 2004/005307). Furthermore, processes for direct asymmetric hydrogenation using transition metal-ligand complexes are disclosed in EP-A 0 647 648, EP-A 0 926 152, EP-A 0 945 457, EP-A 0 955 303 and WO-A 02/40492.

Huiling et al. describe a preparation of (S)-(−)-3-N-methylamino-1-(2-thienyl)-1-propanol from thiophene. Thiophene is converted with 3-chloropropanoyl chloride in the presence of tin tetrachloride in benzene to 3-chloro-1-(2-thienyl)-1-propanone, which is reduced with sodium borohydride in ethanol to 3-chloro-1-(2-thienyl)-1-propanol. Kinetic resolution by transesterification using vinyl butanoate and lipase B from *Candida antarctica* as catalyst in hexane yielded (S)-3-chloro-1-(2-thienyl)-1-propanol, which is converted to (S)-3-iodo-1-(2-thienyl)-1-propanol using sodium iodide in acetone. Subsequent treatment with methylamine in tetrahydrofuran afforded (S)-(−)-3-N-methylamino-1-(2-thienyl)-1-propanol.

Sorbera et al. describe another preparation of (S)-(−)-3-N-methylamino-1-(2-thienyl)-1-propanol from thiophene, which is essentially the same as the one described by Huiling et al. except that 3-chloro-1-(2-thienyl)-1-propanone is asymmetrically reduced to (S)-3-chloro-1-(2-thienyl)-1-propanol using borane and catalytic amounts of (R)-3,3-diphenyl-1-methyltetrahydro-3H-pyrrolo[1,2-c][1,3,2]oxazaborole in THF. This asymmetric reduction afforded (S)-3-chloro-1-(2-thienyl)-1-propanol in a yield of 86% from 3-chloro-1-(2-thienyl)-1-propanone (Wheeler et al. *J. Label. Compd. Radiopharm.* 1995, 36, 213-223).

The drawbacks of the preparations of (S)-(−)-3-N-methylamino-1-(2-thienyl)-1-propanol above, are the use of toxic or carcinogenic compounds such as tin tetrachloride and benzene and/or the use of expensive compounds such as borane or sodium iodide, the latter being in addition difficult to dispose of The disclosed asymmetric hydrogenation processes with diphosphines are not satisfying in regard of the hydrogenation of 3-N-methylamino-1-(2-thienyl)-1-propanone.

It is an object of the present invention to provide an ecological and economical process for the preparation of enantiomerically pure 1-substituted-3-aminoalcohols, particularly of (S)-(−)- and (R)-(+)-3-N-methylamino-1-(2-thienyl)-1-propanol. It is another object of the present invention to provide new salts of 3-N-methylamino-1-(2-thienyl)-1-propanone and organic acids.

These objects are achieved by the process of the invention.

Provided is a process for the preparation of salts of a carboxylic acid with an aminoalcohol of the formula

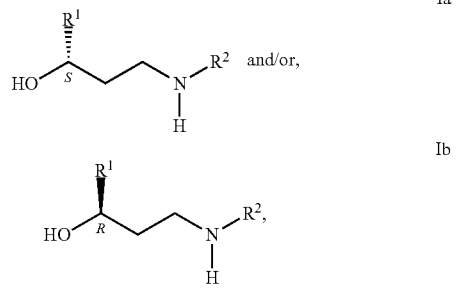

wherein $R^1$ is selected from the group consisting of 2-thienyl, 2-furanyl and phenyl, each optionally substituted with one or more halogen atoms and/or one or more $C_{1-4}$-alkyl or $C_{1-4}$-alkoxy groups, and wherein $R^2$ is $C_{1-4}$-alkyl or phenyl, each optionally substituted with one or more halogen atoms and/or one or more $C_{1-4}$-alkyl or $C_{1-4}$-alkoxy groups, comprising asymmetrically hydrogenating a salt of a carboxylic acid with an aminoketone of the formula

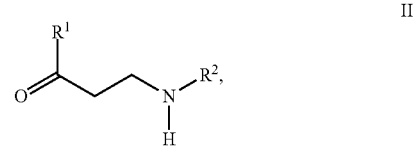

wherein $R^1$ and $R^2$ are as defined above,
in the presence of a transition metal complex of a diphosphine ligand.

In Sakuraba et al., *Chem. Pharm. Bull.* 1995, 43, 748-753, and JP-A 50-70412 the asymmetric hydrogenation of HCl salts of 3-N-methylamino-1-phenyl-1-propanol and 3-amino-1-phenyl-1-propanone is disclosed. EP-A-457559 discloses the preparation of HCl salts of 3-dimethylamino-1-(2-thienyl)-1-propanone and (S)-(−)-N,N-dimethyl-3-(2-thienyl)-3-hydroxypropaneamine as well as the oxalate salts of (5)-(+)-N,N-dimethyl-3-(1-napthalenyloxy)-3-(2-thienyl)-propanamine and (S)-(−)-N,N-dimethyl-3-(1-naphthalenyloxy)-3-(2-thienyl)propanamine. The latter two ones being aromatic ethers of the compounds of formula I. Direct preparation of the respective organic acid salts is not disclosed in the prior art. Surprisingly, these compounds can be used in the hydrogenation reaction as well without increasing the amount of by-products. Using organic acids is favourable, since they are less acidic than HCl and therefore the risk of decomposition while concentrating during recovery of the products is reduced. The compounds obtainable by the present process can be used directly without exchange of the anion.

In a preferred embodiment, the diphosphine ligand is

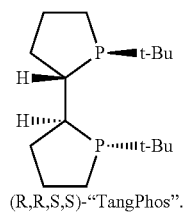

(R,R,S,S)-"TangPhos".

Asymmetric hydrogenation of 1-substituted-3-N-alkylamino-1-propanone hydrochlorides with diphosphine-transition metal complexes is not possible without generating the free amines by neutralizing the acidic salts. Due to the fact that the free 1-substituted-3-N-alkylamino-1-propanones tend to decompose, the resulting 1-substituted-3-N-alkylamino-1-propanols are contaminated with by-products. Exchanging the hydrochloric acid with a carboxylic acid allows direct hydrogenation of the resulting, optionally purified, salt of a 1-substituted-3-N-alkylmino-1-propanone in high yields, high purity and high enantiomeric excess (ee). Avoiding decomposition of the free aminoketone in the presence of base is another advantageous feature of the present invention.

Carboxylic acids in the meaning of the present invention are carboxylic acids having one free carboxyl group which can form a salt with an amino compound of formulae II and/or I. Particularly preferred carboxylic acids are monocarboxylic acids. Dicarboxylic or tricarboxylic acids which do not form an inner salt like fumaric, maleic or adipic acid tend to give unusable resinous precipitates. However, carboxylic acids which form an inner salt and still have one free carboxy group are comprised in the definition of carboxylic acids in the meaning of the present invention. Examples of said carboxylic acids having more than one carboxy group, but having only one free carboxy group, are amino acids such as aspartic acid or glutamic acid.

In a preferred process, the carboxylic acid is selected from the group consisting of optionally substituted $C_{1-18}$-alkanoic acids and optionally substituted mono- and bicyclic aromatic acids.

In a preferred embodiment the carboxylic acids are substituted with one or more $C_{1-6}$-alkyl, $C_{1-6}$-alkoxy, aryl, amino, optionally protected carbonyl, halogen or hydroxy groups and optionally further carboxylic groups.

Examples for $C_{1-18}$-alkanoic acids in the meaning of the present process are butyric acid, valeric acid, caproic acid, pelargonic acid, lauric acid, palmitic acid, stearic acid, 2-hydroxybutyric acid, 3-hydroxy-3-methylbutyric acid, 2-hydroxy-4-phenylbutyric acid, L-aspartic acid, D-aspartic acid, DL-aspartic acid, 2-keto-L-gulonic acid, 2-keto-D-gulonic acid, (−)-2,3:4,6-di-O-isopropylidene-2-keto-L-gulonic acid and (+)-2,3:4,6-di-O-isopropylidene-2-keto-D-gulonic acid.

In a further preferred process the carboxylic acid is a mono- or bicyclic aromatic acid, optionally substituted with one or more $C_{1-6}$-alkyl, $C_{1-6}$-alkoxy, halogen or hydroxy groups.

Examples for mono- and bicyclic aromatic carboxylic acids in the meaning of the present process are benzoic acid, salicylic acid, 3-methyl-benzoic acid and 1-, or 2-naphthalene-carboxylic acid.

Here and hereinbelow the term "enantiomerically pure compound" comprises optically active compounds with an enantiomeric excess (ee) of at least 90%.

Here and hereinbelow the term "$C_{1-n}$-alkyl", for example "$C_{1-6}$-alkyl", represents a linear or branched alkyl group having 1 to n carbon atoms. Optionally with one or more halogen atoms substituted $C_{1-6}$-alkyl represents for example methyl, ethyl, propyl, isopropyl, butyl, isobutyl, sec-butyl, tert-butyl, pentyl and hexyl.

Here and hereinbelow the term "$C_{1-n}$-alkoxy", for example "$C_{1-6}$-alkoxy", represents a linear or branched alkoxy group having 1 to n carbon atoms. Optionally with one or more halogen atoms substituted $C_{1-6}$-alkoxy represents for example methoxy, ethoxy, propoxy, isopropoxy, butoxy, isobutoxy, sec-butoxy, tert-butoxy, pentyloxy and hexyloxy.

Here and hereinbelow the term "$C_{3-n}$-cycloalkyl", for example "$C_{3-10}$-cycloalkyl", represents a cycloaliphatic group having 3 to n carbon atoms. Optionally with one or more halogen atoms substituted $C_{3-10}$-cycloalkyl represents for example mono- and polycyclic ring systems such as cyclopropyl, cyclobutyl, cyclopentyl, cyclohexyl, cycloheptyl, cyclooctyl, adamantyl or norbornyl.

Here and hereinbelow the term "$C_{3-n}$-cycloalkoxy", for example "$C_{3-10}$-cycloalkoxy" represents a cycloalkoxy group having 3 to n carbon atoms. Optionally with one or more halogen atoms subtituted $C_{3-10}$-cycloalkyl represents for example cyclopropoxy, cyclobutoxy, cyclopentyloxy, cyclohexyloxy, cycloheptyloxy, cyclooctyloxy and cyclodecyloxy.

Here and hereinbelow the term "aryl" represents an aromatic group, preferably phenyl or naphthyl, optionally being substituted with one or more halogen atoms, nitro and/or amino groups, and/or optionally substituted $C_{1-6}$-alkyl, $C_{1-6}$-alkoxy or di-$C_{1-6}$-alkylamino groups, wherein the alkyl moieties optionally are substituted with one or more halogen atoms.

In a preferred embodiment $R^1$ is 2-thienyl, optionally substituted with one or more halogen atoms, and $R^2$ is methyl or ethyl.

In a further preferred embodiment, the compound of formula Ia and/or Ib is selected from the group consisting of (S)-(−)-3-N-methylamino-1-(2-thienyl)-1-propanol, (S)-(−)-3-N-methylamino-1-(3-chloro-2-thienyl)-1-propanol, (R)-(+)-3-N-methylamino-1-(2-thienyl)-1-propanol and (R)-(+)-3-N-methylamino-1-(3-chloro-2-thienyl)-1-propanol.

In a preferred process, the transition metal is selected from the group consisting of rhodium, ruthenium and iridium, preferably rhodium.

In a further preferred process, the diphosphine ligand is selected from the group consisting of

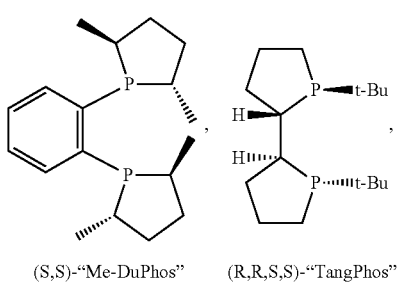

(S,S)-"Me-DuPhos"   (R,R,S,S)-"TangPhos"

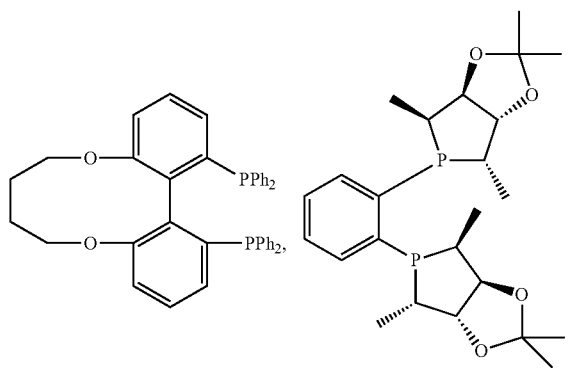

(S)-C4-"TunePhos",   (S,S,S,S)-"Me-KetalPhos",

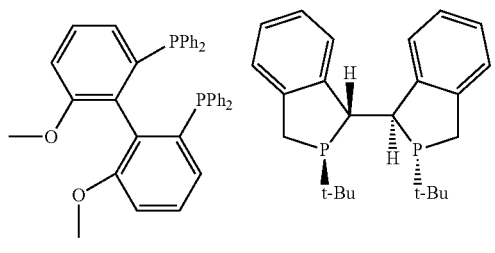

(S) and (R)-"MeO-BiPhep" and "($R_P,R_P,S_C,S_C$)-DuanPhos".

All mentioned ligands are commercially available, e.g. from Chiral Quest, Inc, Monmouth Junction, N.J., USA.

In a preferred process, the compounds of formulae Ia and Ib are obtained from their corresponding salts with a carboxylic acid by aqueous hydrolysis in the presence of an alkali or earth alkali hydroxide.

Provided are salts of a carboxylic acid with an aminoketone of the formula

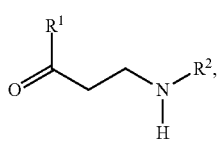

II wherein $R^1$ is selected from the group consisting of 2-thienyl, 2-furanyl and phenyl, each optionally substituted with one or more halogen atoms and/or one or more $C_{1-4}$-alkyl or $C_{1-4}$-alkoxy groups, and wherein $R^2$ is $C_{1-4}$-alkyl or phenyl, each optionally substituted with one or more halogen atoms and/or one or more $C_{1-4}$-alkyl or $C_{1-4}$-alkoxy groups.

Particularly preferred, the carboxylic acid is selected from the group consisting of $C_{1-18}$-alkanoic acids, (−)-2,3:4,6-di-O-isopropylidene-2-keto-L-gulonic acid, (+)-2,3:4,6-di-O-isopropylidene-2-keto-D-gulonic acid, 2-keto-L-gulonic acid, 2-keto-D-gulonic acid, L-aspartic acid, D-aspartic acid, benzoic acid, 3-methylbenzoic acid, salicylic acid and 2-naphthalenecarboxylic acid.

Furthermore provided are salts of a carboxylic acid with an aminoalcohol of the formula

I wherein $R^1$ is selected from the group comprising 2-thienyl, 2-furanyl and phenyl, each optionally substituted with one or more halogen atoms and/or one or more $C_{1-4}$-alkyl or $C_{1-4}$-alkoxy groups, and wherein $R^2$ is $C_{1-4}$-alkyl or phenyl, each optionally substituted with one or more halogen atoms and/or one or more $C_{1-4}$-alkyl or $C_{1-4}$-alkoxy groups, with the exception of salts wherein the acid is (−)-2,3:4,6-di-O-isopropylidene-2-keto-L-gulonic acid or (+)-2,3:4,6-di-O-isopropylidene-2-keto-D-gulonic acid.

The present invention is illustrated by the following non-limiting examples.

EXAMPLES

Example 1

Preparation of 3-N-methylamino-1-(2-thienyl)-1-propanone hydrochloride (PRON-HCl)

A mixture of 2-acetylthiophene (25.5 g, 200 mmol), methylamine hydrochloride (14.9 g, 220 mmol), paraformaldehyde (8.2 g, 280 mmol) and ethanol (100 mL) is heated in an autoclave at 120 to 130° C. for 9 h. The obtained light brown solution is cooled to 20° C. and part of the ethanol (50 mL) is removed by distillation in vacuo. Ethyl acetate (200 mL) is added to the residue to afford a thick suspension, which is cooled to 0° C. and kept for 45 min at that temperature. The obtained precipitate is isolated by filtration and dried, yielding 29.3 g 3-N-methylamino-1-(2-thienyl)-1-propanone hydrochloride (PRON-HCl, 71%) as a slightly yellow powder.

Comparative Example 1

Preparation of racemic 3-N-methylamino-1-(2-thienyl)-1-propanol (PROL-HCl)

Sodium hydroxide (4.0 g of a 50% aqueous solution) is added to a mixture of PRON-HCl (10.3 g, 50 mmol) and ethanol (35 mL) at 4° C. in about 5 min. Neat sodium borohydride (0.95 g, 25 mmol) is added in several portions in about 30 min to afford a beige suspension which is stirred at 4° C. for additional 4 h. Acetone (10 mL) is added dropwise in 5 min and the mixture is stirred for additional 10 min before water (20 mL) is added. The mixture is concentrated about 5 times in vacuo and the obtained residue is extracted with tert-butyl methyl ether (MTBE) (2×20 mL). The collected organic phases are concentrated in vacuo affording 7.2 g racemic 3-N-methylamino-1-(2-thienyl)-1-propanol (PROL-HCl 84%) as an orange oil which crystallizes spontaneously after a few h. $^1$H-NMR (DMSO-$d_6$, 400 MHz): 7.35 (1H, dd, J=4.8, 1.0), 6.94 (1H, dd, J=4.8, 3.6), 6.90 (1H, dd, J=3.6, 1.0), 4.90 (1H, t), 3.7 (2H, m), 2.56 (2H, m), 2.25 (3H, s), 1.79 (2H, q); $^{13}$C-NMR (DMSO-$d_6$, 100 MHz): 150.9, 126.3, 123.7, 122.3, 67.8, 48.5, 38.7, 36.0.

Comparative Example 2

Preparation of (S)-(−)-3-N-methylamino-1-(2-thienyl)-1-propanol ((S)-PROL-HCl)

In a 50 mL autoclave a solution of PRON-HCl (250 mg, 0.56 mmol) in methanol (5 mL) and an equivalent amount of NaOH mixture is charged under nitrogen. Afterwards, a solution of [Rh((S,S)-Me-Duphos)]BF$_4$ (2.7 mg) in methanol (2 mL) prepared under nitrogen is added via a syringe. The autoclave is then closed and purged several times with nitrogen, heated up to 50° C., then hydrogen is added until the pressure reaches 30 bar. After 5 h at that temperature under stirring, the autoclave is cooled to room temperature. Once cold, the clear yellow-brownish solution is transferred into a 50 mL round bottom flask and concentrated to dryness affording a beige solid (0.23 g, 92%, ee: about 97% by HPLC).

Comparative Example 3

Preparation of (S)-PROL

A solution of PRON-HCl (250 mg, 0.56 mmol) in methanol (5 mL) is charged under nitrogen in a 50 mL autoclave. Afterwards, a solution of 1.8 mg Rh(cod)$_2$BF$_4$ and 2.7 mg the ligand of formula III, with R$^3$=OMe, R$^4$=R$^5$=dicyclohexylphosphinyl and R$^6$=R$^7$=diphenylphosphinyl, in methanol (2 mL) previously prepared by stirring the components for 15 min under nitrogen is added via a syringe. The hydrogenation is carried out as described above, affording (S)-PROL as a beige solid (0.21 g, 84%, ee: about 11% by HPLC)

Example 2

Preparation of 3-N-methylamino-1-(2-thienyl)-1-propanone and its (−)-2,3:4,6-di-O-isopropylidene-2-keto-L-gulonic acid salt (PRON-diketegulac)

A mixture of PRON-HCl (15.0 g, 47.5 mmol), MTBE (170 mL) and water (20 mL) is cooled to 0° C., then sodium hydroxide (12.8 g of a 20% aqueous solution) is added dropwise in 15 min and stirred for 10 min. Afterwards, the stirring is stopped, the two phases are separated and the organic one is washed with water (60 mL). Then the collected aqueous phases are extracted with MTBE (2×50 mL). To the two collected organic layers is then added dropwise a solution of (−)-2,3:4,6-di-O-isopropylidene-2-keto-L-gulonic acid ((−)-DAG, 13.1 g, 4.48 mol) in MTBE (400 mL). The product precipitates already during addition. At the end of the addition, the suspension is concentrated in vacuo to half the volume, the residue is heated to 50 to 60° C. and heptane (250 mL) is added. Afterwards, the suspension is cooled down to 5° C., the precipitate is filtered off and washed with MTBE/heptane (1:2, v:v, 2×60 mL). Drying at 30° C. for 15 h at 30 mbar affords a white solid (13.2 g, 66%). (assay is 96.1 weight %, purity is 99.6 area %, by HPLC)

Example 3

Preparation of PRON-diketegulac

A sticky suspension of 675 g (2.13 mol) PRON-HCl in 5.5 L MTBE and 0.9 L water is stirred at a temperature of 0 to 5° C. in a 10 L vessel. Within 0.5 h 576 g (2.88 mol) of a 20% NaOH-solution are added and the reaction mixture is stirred for another 30 min at the same temperature. After phase separation and washing of the organic phase with water (1.3 L) and extracting the aqueous phase with MTBE (2×1.3 L), the combined organic layers are cooled in a 10 L vessel to below 10° C. After addition of a solution of 590 g (−)-DAG (2.02 mol) within 15 min a yellowish mixture is obtained and crystallization occurs spontaneously or after addition of a crystallization aid, such as a small crystal of the product. After further stirring for 2 h at 0 to 5° C., filtration, washing with MTBE (2×1.5 L) and drying in vacuo at 50 to 55° C., the product (740 g of off-white solid matter) is obtained.

Example 4

Recrystallization of PRON-diketegulac

A suspension of 738 g of the product of example 3, 5.3 L MTBE and 2.7 L methanol are heated under reflux. After addition of further 1.8 L methanol at the same temperature a clear yellowish solution is obtained. During cooling to 0 to 5° C. within 3 h, the product precipitates. After further stirring at 0 to 5° C. for 2 h, filtration, washing with MTBE (2×1 L) and drying in vacuo at 50 to 55° C., the product (538 g of white solid) is obtained.

Example 5

Hydrogenation of (S)-PRON-diketegulac

A solution of PRON-diketegulac of example 4 (250 mg, 0.56 mmol) in methanol (5 mL) is charged under nitrogen in a 50 mL autoclave. A solution of [Rh((R,R,S,S)-Tangphos)-(norbornadiene)]BF$_4$ (3 mg) in methanol (2 mL) is added via a syringe to the first mixture. The hydrogenation is carried out as described above, affording the salt of (S)-(−)-3-N-methylamino-1-(2-thienyl)-1-propanol and (−)-DAG ((S)-PROL-diketegulac) as a beige solid (0.22 g, 92%). Conversion is 100% by HPLC, ee is 95% (S isomer id preferably formed).

Example 6

Hydrolysis of (S)-PROL-diketegulac 9.0 g (20.2 mmol) of solid PROL-diketegulac of example 5 is added in portions to a mixture of water (22 mL), CH$_2$Cl$_2$ (18 mL) and an aqueous solution of sodium hydroxide (30%, 2.07 g, 25.9 mmol) and the reaction mixture (two phases) is stirred for 15 min. After phase separation, the aqueous phase is extracted with CH$_2$Cl$_2$ (12 mL). The combined organic phases are washed with water (13 mL). The solvent is removed at 20° C. in vacuo to a volume of 9 mL. Heptane (18 mL) is added to the residue and the resulting solution is further concentrated to about 18 mL in vacuo at 20° C. Crystallization occurs spontaneously or after seeding and the suspension is further stirred for 30 min at 20° C. The precipitate is filtrated, washed with heptane (7 mL) and dried at 40° C. for 15 h at 25 mbar affording (S)-PROL (3.0 g of white solid, 87%).

Example 7

Preparation of PRON-2-keto-L-gulonate

A mixture of 15.0 g (47.5 mmol) PRON-HCl, 170 mL MTBE and 20 mL water is cooled to 5 to 10° C. in a 250 mL vessel. After addition of 12.8 g of a 20% NaOH solution the mixture is stirred for further 15 min, while phase separation occurs. The organic phase is washed with water (60 mL) and the aqueous phase is extracted with MTBE (2×50 mL). The combined organic phases are cooled to below 10° C. and within 15 min a suspension of 8.7 g (45 mmol) 2-keto-L-gulonic acid in 400 mL MTBE is added. A sticky suspension is formed. The volume of the solvent is reduced to approximately the half. The reaction mixture is heated under reflux and 250 mL heptane are added. After further addition of 300 mL methanol and heating under reflux for 30 min, the mixture is cooled to room temperature (RT) and the solvent is removed. The resinous residue is mixed with 100 mL methanol and the solid matter is filtered off and dried in vacuo at 50 to 55° C. to yield 8.3 g tan solid matter.

Example 8

Recrystallization of PRON-2-keto-L-gulonate 8.2 g solid product of example 7 is heated under reflux with 100 mL ethanol. Under stirring, the clear solution is cooled to RT and a resin deposits. The mixture is stirred for 1 hour at RT. The moist resin is dried in vacuo at 50 to 55° C. to afford 4.5 g of tan solid matter.

Example 9

Preparation of PRON-Benzoate

A mixture of 15.0 g (47.5 mmol) PRON-HCl, 170 mL MTBE and 20 mL water is cooled to 5 to 10° C. in a 250 mL vessel. After addition of 12.8 g of a 20% NaOH solution the mixture is stirred for further 15 min, while phase separation occurs. The organic phase is washed with water (60 mL) and the aqueous phase is extracted with MTBE (2×50 mL). The combined organic phases are cooled to below 10° C. and within 15 min a suspension of 5.5 g (45 mmol) benzoic acid in 400 mL MTBE is added. An oily suspension is formed. The volume of the solvent is reduced to approximately the half. The reaction mixture is heated under reflux and 250 mL heptane are added. The mixture is cooled to RT and stirred for 1 hour. The solid matter is filtered off, washed with Heptane/MTBE (2×60 mL) and dried in vacuo at 50 to 55° C. Yield: 10.4 g yellow-brown solid product.

Example 10

Recrystallization of PRON-benzoate 10.3 g solid product of example 9 is heated under reflux with 50 mL ethylacetate. Under stirring, the clear solution is cooled to RT and a solid deposits. The mixture is stirred for 1 hour at RT. The resin is dried in vacuo at 50 to 55° C. which affords 6.1 g of light tan solid matter.

Example 11

Hydrogenation of PRON-benzoate

A solution of PRON-benzoate of example 10 (146 mg) in methanol (5 mL) is charged under nitrogen in a 50 mL autoclave. Afterwards, a solution of 3 mg [Rh((S,S)-Me-Duphos)-(1,4-cyclooctadiene)]BF$_4$ in methanol (2 mL) is added via a syringe. The mixture is hydrogenated as described above affording 0.12 g solid product ((S)-PROL-benzoate). Conversion is 99% by HPLC, ee is 96.7%, S isomer preferably formed.

Comparative Example 4

Preparation of PRON-p-toluenesulfonate

A mixture of 15.0 g (47.5 mmol) PRON-HCl, 170 mL MTBE and 20 mL water is cooled to 5 to 10° C. in a 250 mL vessel. After addition of 12.8 g of a 20% NaOH solution the mixture is stirred for further 15 min, while phase separation occurs. The organic phase is washed with water (60 mL) and the aqueous phase is extracted with MTBE (2×50 mL). The combined organic phases are cooled to below 10° C. and within 15 min a suspension of 8.6 g (45 mmol) p-toluenesulfonic acid monohydrate in 400 mL MTBE is added. An oily suspension is formed. The volume of the solvent is reduced to approximately the half. The reaction mixture is heated under reflux and 250 mL heptane are added. The mixture is cooled to RT and stirred for 30 min. The solid matter is filtered off, washed with MTBE (2×60 mL) and dried in vacuo at 50 to 55° C. affording 14.3 g of product (tan solid matter).

Comparative Example 5

Recrystallization of PRON-p-toluenesulfonate 14.2 g solid product of comparative example 4 is heated under reflux with 50 mL isopropanol. Under stirring, the clear solution is cooled to RT and a solid deposits. The mixture is stirred for 1 hour at RT. The resin is dried in vacuo at 50 to 55° C. which affords 12.5 g of tan solid matter.

Comparative Example 6

Hydrogenation of PRON-p-toluenesulfonate

A solution of PRON-p-toluenesulfonate of comparative example 5 (155 mg) in methanol (5 mL) is charged under nitrogen in a 50 mL autoclave. Afterwards, a solution of 3 mg [Rh(Me-Duphos)(1,4-cyclooocatadiene)]BF$_4$ in methanol (2 mL) is added via a syringe. The hydrogenation is carried out as described above, affording 0.12 g solid product ((S)-PROL-p-toluenesulfonate). Conversion is 5% by HPLC, ee is >90%, S isomer preferably formed.

Example 12

Preparation of PRON-laurate

A mixture of 15.0 g (47.5 mmol) PRON-HCl, 170 mL MTBE and 20 mL water is cooled to 5 to 10° C. in a 250 mL vessel. After addition of 12.8 g of a 20% NaOH solution the mixture is stirred for further 15 min, while phase separation occurs. The organic phase is washed with water (60 mL) and the aqueous phase is extracted with MTBE (2×50 mL). The combined organic phases are cooled to below 10° C. and within 15 min a suspension of 9.0 g (45 mmol) dodecanoic acid in 200 mL MTBE is added. After 1 hour stirring no product has solidified. The solvent is removed in vacuo and the oily residue is solved in 50 mL acetonitrile and heated under reflux. The mixture is cooled to RT and stirred for 30 min. At first an oil secretes, which crystallizes at a temperature of below 30° C. The suspension is further stirred for 30 min at RT, than 30 mL acetonitrile are added to the thickened suspension. The solid matter is filtered off, washed with cold acetonitrile (2×10 mL) and dried in vacuo at below 30° C., affording 10.9 g product. Yield: 10.9 g white solid matter.

Example 13

Recrystallization of PRON-laurate 10.7 g solid product of example 12 is heated under reflux with 70 mL acetonitrile. Under stirring, the clear solution is cooled to RT and an oil secrets, which crystallizes at below 30° C. The mixture is stirred for 30 min at 10 to 15° C. and 30 mL acetonitrile are added to the thickened suspension. The solid matter is filtered off, washed with cold acetonitrile (2×20 mL) and dried in vacuo at below 30° C. Yield: 6.3 g white solid matter.

Example 14

Hydrogenation of PRON-laurate

A solution of PRON-laurate of example 13 (184 mg) in methanol (5 mL) is charged under nitrogen in a 50 mL autoclave. Afterwards, a solution of 3 mg [Rh((R,R,S,S)-Tangphos)(norbornadiene)]BF$_4$ in methanol (2 mL) is added via a syringe. The mixture is hydrogenated as described above, affording 0.16 g solid product ((S)-PROL-laurate). Conversion is 100% by HPLC, ee is 93.6%, S isomer preferably formed.

The invention claimed is:

1. A salt of a carboxylic acid with an aminoketone of the formula;

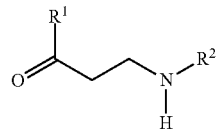

II wherein $R^1$ is 2-thienyl or 2-furanyl, each optionally substituted with one or more halogen and/or one or more $C_{1-4}$-alkyl or $C_{1-4}$-alkoxy, and wherein $R^2$ is $C_{1-4}$-alkyl or phenyl, each optionally substituted with one or more halogen and/or one or more $C_{1-4}$-alkyl or $C_{1-4}$-alkoxy wherein the carboxylic acid is selected from the group consisting of $C_{1-18}$-alkanoic acids, (−)-2,3:4,6-di-O-isopropyl-idene-2-keto-L-gulonic acid, (+)-2,3:4,6-di-O-isopropylidene-2-keto-D-gulonic acid, 2-keto-L-gulonic acid, 2-keto-D-gulonic acid, L-aspartic acid, D-aspartic acid, DL-aspartic acid, benzoic acid, 3-methyl-benzoic acid, salicylic acid and 1-naphthanelenecarboxylic acid and 2-naphthalenecarboxylic acid.

* * * * *